(12) United States Patent
Mokhtari et al.

(10) Patent No.: US 8,460,584 B2
(45) Date of Patent: Jun. 11, 2013

(54) CARBOXYLIC ACID STABILIZED SILVER NANOPARTICLES AND PROCESS FOR PRODUCING SAME

(75) Inventors: Mahya Mokhtari, Toronto (CA); Marko Saban, Toronto (CA); Roger Earl Gaynor, Oakville (CA)

(73) Assignee: Xerox Corporation, Norwalk, CT (US)

( * ) Notice: Subject to any disclaimer, the term of this patent is extended or adjusted under 35 U.S.C. 154(b) by 450 days.

(21) Appl. No.: 12/250,727

(22) Filed: Oct. 14, 2008

(65) Prior Publication Data

US 2010/0090179 A1    Apr. 15, 2010

(51) Int. Cl.
*H01B 1/02* (2006.01)

(52) U.S. Cl.
USPC ............... 252/514; 252/500; 75/343; 75/351; 75/371; 106/31.92; 257/347; 423/23

(58) Field of Classification Search
USPC .. 252/500, 514; 75/343, 351, 371; 106/31.92; 423/23; 257/347
See application file for complete search history.

(56) References Cited

U.S. PATENT DOCUMENTS

| | | | |
|---|---|---|---|
| 6,660,058 B1 * | 12/2003 | Oh et al. | 75/351 |
| 6,878,184 B1 * | 4/2005 | Rockenberger et al. | 75/343 |
| 7,270,694 B2 | 9/2007 | Li et al. | |
| 7,306,969 B2 | 12/2007 | Wu et al. | |
| 7,737,497 B2 * | 6/2010 | Li | 257/347 |
| 7,744,834 B2 * | 6/2010 | Lee et al. | 423/23 |
| 2004/0247690 A1 * | 12/2004 | Yang | 424/490 |
| 2005/0129843 A1 | 6/2005 | Wu et al. | |
| 2007/0039417 A1 * | 2/2007 | Huang et al. | 75/371 |
| 2007/0099357 A1 | 5/2007 | Li et al. | |
| 2008/0041270 A1 * | 2/2008 | Lee et al. | 106/31.92 |
| 2008/0085594 A1 | 4/2008 | Li et al. | |

FOREIGN PATENT DOCUMENTS

EP     1579935 A1  *  9/2005
JP     2007-154292  *  6/2007

OTHER PUBLICATIONS

Y. Wu, Y. Li, and B. S. Ong, "Printed Silver Ohmic Contacts for High-Mobility Organic Thin-Film Transistors", J. Am. Chem. Soc., vol. 128, 4202-4203, (2006).*
Lin et al., "Direct Synthesis of Narrowly Dispersed Silver Nanoparticles Using a Single-Source Precursor", Sep. 2003, American Chemical Society, 19, pp. 10081-10085.*
Lee et al., "Environmentally friendly synthesis of organic-soluble silver nanoparticles for printed electronics", *Nanotechnology*, 18, 2007, 335601, pp. 1-5, IOP Publishing Ltd.

* cited by examiner

*Primary Examiner* — Khanh Tuan Nguyen
(74) *Attorney, Agent, or Firm* — Fay Sharpe LLP

(57) ABSTRACT

Processes for producing carboxylic acid-stabilized silver nanoparticles are disclosed. The processes comprise (a) forming a suspension of silver salt particles in a carboxylic acid; (b) forming a solution of an organohydrazine and a first organic solvent; (c) heating the suspension; (d) adding the solution to the suspension to form a mixture; and (e) reacting the mixture to form carboxylic acid-stabilized silver nanoparticles.

28 Claims, 3 Drawing Sheets

CARBOXYLIC ACID STABILIZED SILVER NANOPARTICLES AND PROCESS FOR PRODUCING SAME

BACKGROUND

Disclosed herein, in various embodiments, are stable, high performing nanoparticle compositions as well as processes and devices for making and/or using the same.

Fabrication of electronic circuit elements using liquid deposition techniques may be beneficial as such techniques provide potentially low-cost alternatives to conventional mainstream amorphous silicon technologies for electronic applications such as thin film transistors (TFTs), light-emitting diodes (LEDs), RFID tags, photovoltaics, etc. However, the deposition and/or patterning of functional electrodes, pixel pads, and conductive traces, lines and tracks which meet the conductivity, processing, and cost requirements for practical applications have been a great challenge. The metal, silver, is of particular interest as conductive elements for electronic devices because silver is much lower in cost than gold and it possesses much better environmental stability than copper.

Prior lab-scale methods for producing silver nanoparticles used multiple steps and were laborious and time-consuming. In addition, the resultant product typically manifested as a sticky paste, raising handling issues. Furthermore, the results were not reproducible or easily scaled up. For example, one method produced silver nanoparticles in the presence of oleylamine, then substituted the oleylamine with oleic acid through a ligand exchange process. However, the exchange process is not 100% efficient and the remaining oleylamine can be considered an impurity.

There is therefore a critical need, addressed by embodiments of the present disclosure, for lower cost methods for preparing liquid processable, stable silver-containing nanoparticle compositions that are suitable for fabricating electrically conductive elements of electronic devices.

BRIEF DESCRIPTION

The present application discloses, in various exemplary embodiments, processes for preparing silver-containing nanoparticle compositions, as well as the compositions so produced. Devices which use the nanoparticle compositions, such as thin film transistors, are also disclosed.

Disclosed in embodiments are processes for producing carboxylic acid-stabilized silver nanoparticles, comprising:
forming a suspension of silver salt particles in a carboxylic acid;
forming a solution of an organohydrazine and a first organic solvent;
heating the suspension;
adding the solution to the suspension to form a mixture; and
reacting the mixture to form carboxylic acid-stabilized silver nanoparticles.

The silver salt may be selected from the group consisting of silver acetate, silver nitrate, silver oxide, silver acetylacetonate, silver benzoate, silver bromate, silver bromide, silver carbonate, silver chloride, silver citrate, silver fluoride, silver iodate, silver iodide, silver lactate, silver nitrite, silver perchlorate, silver phosphate, silver sulfate, silver sulfide, and silver trifluoroacetate.

The carboxylic acid may have from 4 to about 20 carbon atoms. The carboxylic acid can be selected from the group consisting of butyric acid, pentanoic acid, hexanoic acid, heptanoic acid, octanoic acid, nonanoic acid, decanoic acid, undecanoic acid, dodecanoic acid, tridecanoic acid, myristic acid, pentadecanoic acid, palmitic acid, heptadecanoic acid, stearic acid, oleic acid, nonadecanoic acid, icosanoic acid, eicosenoic acid, elaidic acid, linoleic acid, and palmitoleic acid.

The organohydrazine may be of the formula:

$$R^6R^7N-NR^8R^9$$

wherein $R^6$, $R^7$, $R^8$ and $R^9$ are independently selected from hydrogen, alkyl, and aryl; and wherein at least one of $R^6$, $R^7$, $R^8$ and $R^9$ is not hydrogen. An exemplary organohydrazine is phenylhydrazine.

The first organic solvent can be selected from the group consisting of toluene, heptane, hexane, benzene, cyclohexane, pentane, bromobenzene, chlorobenzene, and hydrocarbons.

The molar ratio of silver salt to carboxylic acid may be from about 0.01 to about 1. The molar ratio of silver salt to organohydrazine may be from about 0.5 to about 5. The molar ratio of carboxylic acid to organohydrazine may be from about 5 to about 30.

The mixture may be heated at a temperature of from about 50° C. to about 100° C. The mixture may be heated for a period of about 30 minutes or more.

The resulting nanoparticles may have an average diameter of from about 4 nanometers to about 10 nanometers. Alternatively, the resulting nanoparticles may have a particle size distribution of from about 5 nanometers. The resulting nanoparticles may also have a silver content of 80 percent or more.

The process may further comprise the steps of:
separating the silver nanoparticles from the mixture with a non-solvent; and
washing the silver nanoparticles.

The non-solvent may comprise acetone, methanol, ethanol, propanol, isopropanol, methyl ethyl ketone, acetonitrile, isobutyl alcohol, and combinations thereof.

In other embodiments, processes for producing carboxylic acid-stabilized silver nanoparticles are disclosed which comprise:
forming a suspension of silver salt particles in a carboxylic acid having a first temperature;
forming a solution of an organohydrazine and a first organic solvent;
adding the solution to the suspension to form a mixture;
agitating the mixture;
cooling the mixture to a second temperature; and
adding a non-solvent to the mixture to obtain the carboxylic acid-stabilized silver nanoparticles.

The suspension may be formed using silver acetate particles in oleic acid. The first temperature may be about 80° C.

The solution may be formed using phenylhydrazine in toluene. The solution may be added to the suspension over a period of about 30 minutes.

The mixture may be agitated for about 1 hour. The mixture may be maintained at the first temperature during agitation.

The second temperature may be 40° C. or lower. The non-solvent may be a mixture of acetone and methanol.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
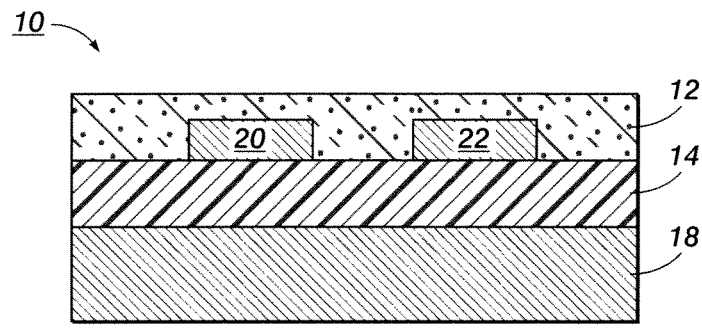
FIG. 1 represents a first embodiment of a thin film transistor containing nanoparticles of the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The term "nano" as used in "silver-containing nanoparticles" indicates a particle size of less than about 1000 nm. In embodiments, the silver-containing nanoparticles have a particle size of from about 0.5 nm to about 1000 nm, from about 1 nm to about 500 nm, from about 1 nm to about 100 nm, and particularly from about 1 nm to about 20 nm. The particle size is defined herein as the average diameter of the silver-containing particles, as determined by TEM (transmission electron microscopy).

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

The processes of the present disclosure produce carboxylic acid-stabilized silver nanoparticles. In some embodiments, the processes comprise (a) forming a suspension of silver salt particles in a carboxylic acid; (b) forming a solution of an organohydrazine and a first organic solvent; (c) heating the suspension; (d) adding the solution to the suspension to form a mixture; and (e) reacting the mixture to form carboxylic acid-stabilized silver nanoparticles. In other embodiments, the processes comprise (a) forming a suspension of silver salt particles in a carboxylic acid having a first temperature; (b) forming a solution of an organohydrazine and a first organic solvent; (c) adding the solution to the suspension to form a mixture; (d) agitating the mixture; (e) cooling the mixture to a second temperature; and (f) adding a non-solvent to the mixture to obtain the carboxylic acid-stabilized silver nanoparticles.

Exemplary silver salts include silver acetate, silver nitrate, silver oxide, silver acetylacetonate, silver benzoate, silver bromate, silver bromide, silver carbonate, silver chloride, silver citrate, silver fluoride, silver iodate, silver iodide, silver lactate, silver nitrite, silver perchlorate, silver phosphate, silver sulfate, silver sulfide, and silver trifluoroacetate. The silver salt particles are desirably fine for homogeneous dispersion in the carboxylic acid, which aids in efficient reaction.

The carboxylic acid used in the suspension has at least 4 carbon atoms. In further specific embodiments, the carboxylic acid has from 4 to about 20 carbon atoms. Exemplary carboxylic acids include butyric acid, pentanoic acid, hexanoic acid, heptanoic acid, octanoic acid, nonanoic acid, decanoic acid, undecanoic acid, dodecanoic acid, tridecanoic acid, myristic acid, pentadecanoic acid, palmitic acid, heptadecanoic acid, stearic acid, oleic acid, nonadecanoic acid, icosanoic acid, eicosenoic acid, elaidic acid, linoleic acid, and palmitoleic acid. In desired embodiments, oleic acid is used.

In embodiments, the molar ratio of silver salt to carboxylic acid is from about 0.01 to about 10, including from about 5 to about 10.

The organohydrazine has the formula:

wherein $R^6$, $R^7$, $R^8$ and $R^9$ are independently selected from hydrogen, alkyl, and aryl; and wherein at least one of $R^6$, $R^7$, $R^8$ and $R^9$ is not hydrogen. In more specific embodiments, the organohydrazine is of the formula $R^6R^7N$—$NH_2$. Exemplary organohydrazines include phenylhydrazine.

The first organic solvent may be toluene, heptane, hexane, benzene, cyclohexane, pentane, bromobenzene, chlorobenzene, and other hydrocarbons. Exemplary organic solvents include high purity isoparaffinic solvents available under the name ISOPAR®. Desirably, the first organic solvent is toluene.

In embodiments, the molar ratio of silver salt to organohydrazine is from about 0.5 to about 5, including from about 1 to about 3. In other embodiments, the molar ratio of carboxylic acid to organohydrazine is from about 5 to about 30, including from about 20 to about 25.

The suspension is at an elevated temperature before the solution is added to the suspension. This first, elevated, temperature may be from about 50° C. to about 100° C. In more specific embodiments, the suspension is heated to a temperature of from about 50° C. to about 80° C. The suspension may be heated for a period of about 30 minutes or more. In more specific embodiments, the suspension is heated for a period of from about 1 hour to about 2 hours. Generally, the suspension is heated at atmospheric pressure. Alternatively, the carboxylic acid, which forms the fluid portion of the suspension, is heated first, and the silver salt particles are then added to the carboxylic acid to form the suspension.

The solution is then added to the suspension to form a mixture. The solution of organohydrazine and first organic solvent does not need to be at an elevated temperature. The addition is typically done at a slow rate to control the amount of foam that is formed from the reduction reaction. For example, the solution may be added to the suspension over a period of about 30 minutes. The suspension may also be agitated, such as by stirring, during the addition of the solution.

The mixture is then reacted to complete the formation of carboxylic acid-stabilized silver nanoparticles. For example, the mixture may be agitated, by stirring or other similar processes. In some embodiments, the reaction/agitation may occur for up to about 1 hour. Generally, the mixture is maintained at the first elevated temperature during the reaction.

The mixture is then cooled down to a second temperature. In particular embodiments, the second temperature may be 40° C. or lower. The silver nanoparticles may then be separated from the reaction mixture by using a non-solvent, i.e. a liquid in which the silver nanoparticles are not soluble, to precipitate the nanoparticles. The silver nanoparticles may then be washed. Exemplary non-solvents include acetone, methanol, ethanol, propanol, isopropanol, methyl ethyl ketone, acetonitrile, isobutyl alcohol, other ketones and alcohols, and combinations thereof. In desirable embodiments, the non-solvent used is a mixture of acetone and methanol (1:1 v/v).

The resulting nanoparticles have an average diameter of 15 nanometers or less. In more specific embodiments, the nanoparticles have an average diameter of from about 1 nanometer to about 10 nanometers, including from about 5 nanometers to about 10 nanometers. This narrow particle size distribution of about 5 to about 10 nanometers between the diameter of the largest nanoparticle and the diameter of the smallest nanoparticle may be desirable in certain situations. These particles of relatively large size, but with small particle size distribution, are better able to disperse when placed in a solvent.

The nanoparticles may have a silver content of 80% or more, including from 80% to about 90%. This content is higher than that produced by conventional processes.

The processes of the present disclosure allow for an inexpensive, one-step process of making carboxylic acid-stabilized silver nanoparticles. The resulting nanoparticles are also pure, in powder form, and can be easily dispersed in toluene. Because they are not in a paste form, they are not sticky, easier to handle, and disperse more homogeneously.

In particular, no organoamine is needed or used in these processes. In contrast, prior methods required multiple steps involving the formation of an amine-stabilized silver nanoparticle, then replacing the amine with a carboxylic acid. Please note that hydrazines are not considered to be amines because they contain an N—N bond, whereas primary, secondary, and tertiary amines contain C—N bonds.

In embodiments, the silver-containing nanoparticles are composed of elemental silver or a silver composite. Besides silver, the silver composite may include either or both of (i) one or more other metals and (ii) one or more non-metals. Suitable other metals include, for example, Al, Au, Pt, Pd, Cu, Co, Cr, In, and Ni, particularly the transition metals, for example, Au, Pt, Pd, Cu, Cr, Ni, and mixtures thereof. Exemplary metal composites are Au—Ag, Ag—Cu, Au—Ag—Cu, and Au—Ag—Pd. Suitable non-metals in the metal composite include, for example, Si, C, and Ge. The various components of the silver composite may be present in an amount ranging for example from about 0.01% to about 99.9% by weight, particularly from about 10% to about 90% by weight. In embodiments, the silver composite is a metal alloy composed of silver and one, two or more other metals, with silver comprising, for example, at least about 20% of the nanoparticles by weight, particularly greater than about 50% of the nanoparticles by weight.

In embodiments, further processing of the silver nanoparticles (with the carboxylic acid on the surface thereof) may occur such as, for example, making them compatible with a liquid deposition technique (e.g., for fabricating an electronic device). Such further processing of the composition may be, for instance, dissolving or dispersing the silver-containing nanoparticles in an appropriate liquid.

The fabrication of conductive elements from the silver nanoparticles can be carried out in embodiments using any suitable liquid deposition technique including i) printing such as screen/stencil printing, stamping, microcontact printing, ink jet printing and the like, and ii) coating such as spin-coating, dip coating, blade coating, casting, dipping, and the like. The deposited silver nanoparticles at this stage may or may not exhibit electrical conductivity.

Heating the deposited nanoparticles at a temperature of below about 300° C., preferably at or below about 250° C. causes them to coalesce to form electrically conductive layers which are suitable for use as conductive elements in electronic devices. The heating is performed for a time ranging from for example about one minute to about 10 hours, particularly from about 5 minutes to about 1 hour. The heating can be done at a temperature of from about 100° C. to about 300° C. In more specific embodiments, the heating is performed at a temperature of from about 150° C. to about 200° C. or from about 170° C. to about 190° C.

The conductivity of the resulting silver-containing elements produced by heating the deposited silver nanoparticles is, for example, at least one thousand S/cm. In other embodiments, the conductivity is at least ten thousand S/cm as measured by four-probe method.

The resulting conductive elements can be used as conductive electrodes, conductive pads, conductive lines, conductive tracks, and the like in electronic devices such as thin film transistor, organic light emitting diodes, RFID (radio frequency identification) tags, photovoltaic, and other electronic devices which require conductive elements or components.

In FIG. 1, there is schematically illustrated a thin film transistor ("TFT") configuration 10 comprised of a heavily n-doped silicon wafer 18 which acts as both a substrate and a gate electrode, a thermally grown silicon oxide insulating dielectric layer 14 on top of which are deposited two metal contacts, source electrode 20 and drain electrode 22. Over and between the metal contacts 20 and 22 is a semiconductor layer 12 as illustrated herein.

Figure 2:
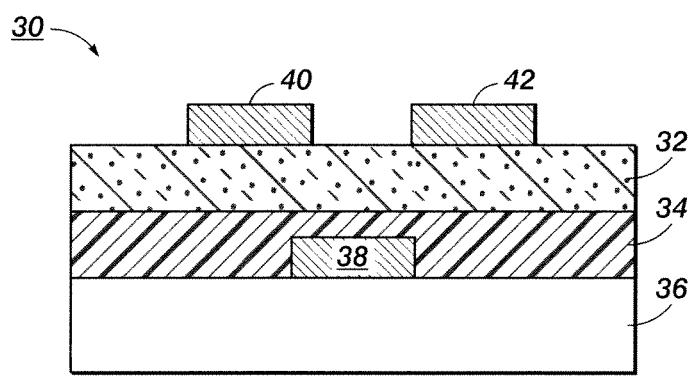
FIG. 2 represents a second embodiment of a thin film transistor containing nanoparticles of the present disclosure.

FIG. 2 schematically illustrates another TFT configuration 30 comprised of a substrate 36, a gate electrode 38, a source electrode 40 and a drain electrode 42, an insulating dielectric layer 34, and a semiconductor layer 32.

Figure 3:
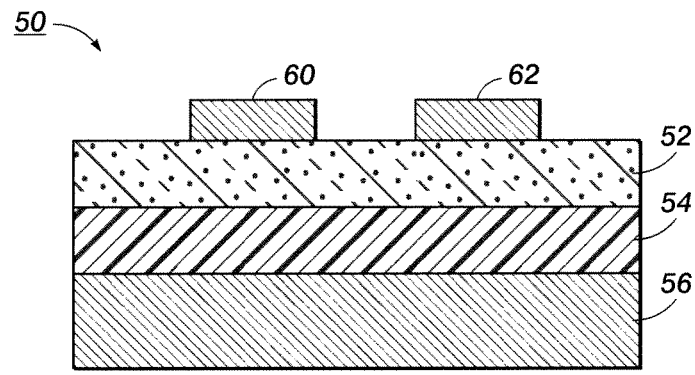
FIG. 3 represents a third embodiment of a thin film transistor containing nanoparticles of the present disclosure.

FIG. 3 schematically illustrates a further TFT configuration 50 comprised of a heavily n-doped silicon wafer 56 which acts as both a substrate and a gate electrode, a thermally grown silicon oxide insulating dielectric layer 54, and a semiconductor layer 52, on top of which are deposited a source electrode 60 and a drain electrode 62.

Figure 4:
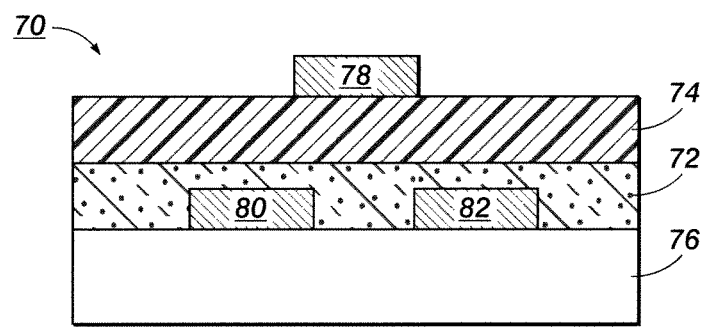
FIG. 4 represents a fourth embodiment of a thin film transistor containing nanoparticles of the present disclosure.

FIG. 4 schematically illustrates an additional TFT configuration 70 comprised of substrate 76, a gate electrode 78, a source electrode 80, a drain electrode 82, a semiconductor layer 72, and an insulating dielectric layer 74.

The substrate may be composed of, for instance, silicon, glass plate, plastic film or sheet. For structurally flexible devices, plastic substrate, such as for example polyester, polycarbonate, polyimide sheets and the like may be used. The thickness of the substrate may be from amount 10 micrometers to over 10 millimeters with an exemplary thickness being from about 50 micrometers to about 2 millimeters, especially for a flexible plastic substrate and from about 0.4 to about 10 millimeters for a rigid substrate such as glass or silicon.

The gate electrode, the source electrode, and the drain electrode are fabricated by embodiments of the present disclosure. The thickness of the gate electrode layer ranges for example from about 10 to about 2000 nm. Typical thicknesses of source and drain electrodes are, for example, from about 40 nm to about 1 micrometer with the more specific thickness being about 60 to about 400 nm.

The insulating dielectric layer generally can be an inorganic material film or an organic polymer film. Illustrative examples of inorganic materials suitable as the insulating layer include silicon oxide, silicon nitride, aluminum oxide, barium titanate, barium zirconium titanate and the like; illustrative examples of organic polymers for the insulating layer include polyesters, polycarbonates, poly(vinyl phenol), polyimides, polystyrene, poly(methacrylate)s, poly(acrylate)s, epoxy resin and the like. The thickness of the insulating layer is, for example from about 10 nm to about 500 nm depending on the dielectric constant of the dielectric material used. An exemplary thickness of the insulating layer is from about 100 nm to about 500 nm. The insulating layer may have a conductivity that is for example less than about $10^{-12}$ S/cm.

Situated, for example, between and in contact with the insulating layer and the source/drain electrodes is the semiconductor layer wherein the thickness of the semiconductor layer is generally, for example, about 10 nm to about 1 micrometer, or about 40 to about 100 nm. Any semiconductor material may be used to form this layer. Exemplary semiconductor materials include regioregular polythiophene, oligthiophene, pentacene, and the semiconductor polymers disclosed in U.S. Pat. Nos. 6,621,099; 6,770,904; and 6,949,762; and "Organic Thin Film Transistors for Large Area Electronics" by C. D. Dimitrakopoulos and P. R. L. Malenfant, *Adv. Mater.*, Vol. 12, No. 2, pp. 99-117 (2002), the disclosures of which are totally incorporated herein by reference. Any suitable technique may be used to form the semiconductor layer. One such method is to apply a vacuum of about $10^{-5}$ to $10^{-7}$ torr to a chamber containing a substrate and a source vessel that holds the compound in powdered form. Heat the vessel until the compound sublimes onto the substrate. The semiconductor layer can also generally be fabricated by solution processes such as spin coating, casting, screen printing, stamping, or jet printing of a solution or dispersion of the semiconductor.

The insulating dielectric layer, the gate electrode, the semiconductor layer, the source electrode, and the drain electrode are formed in any sequence, particularly where in embodiments the gate electrode and the semiconductor layer both contact the insulating layer, and the source electrode and the drain electrode both contact the semiconductor layer. The phrase "in any sequence" includes sequential and simultaneous formation. For example, the source electrode and the drain electrode can be formed simultaneously or sequentially. The composition, fabrication, and operation of thin film transistors are described in Bao et al., U.S. Pat. No. 6,107,117, the disclosure of which is totally incorporated herein by reference. The silver nanoparticles can be deposited as a layer upon any suitable surface, such as the substrate, the dielectric layer, or the semiconductor layer.

The following examples are for purposes of further illustrating the present disclosure. The examples are merely illustrative and are not intended to limit devices made in accordance with the disclosure to the materials, conditions, or process parameters set forth therein.

EXAMPLES

Example 1

178.1 grams of oleic acid (10× molar excess, 90% purity) was preheated to 80° C. in a 0.5 L jacketed reactor under nitrogen blanket. 10 grams of silver acetate (99% purity) was added to the reactor in small portions for better dissolution. The suspension was stirred with a mechanical agitator for 1 hour and became a homogenous white suspension. 1.78 grams of phenylhydrazine (97% purity) in 5 ml of toluene was added to the reactor over a period of 30 minutes. The reaction mixture became dark brown liquid with metallic blue surface indicating the formation of silver nanoparticles. The solution was mixed for an additional hour to ensure completion of the reduction reaction. The reactor was cooled down to below 40° C. A 300 ml mixture of acetone and methanol (1:1 v/v) was added to the reactor over 5 minutes. The solution turned into a black blue liquid. After an additional 5 minutes of mixing, the solution was discharged from the reactor and was transferred over to a vacuum filtration unit (10 cm Buchner funnel with Whatman #5 filter paper (2.5 μm pore size)). 150 ml of methanol was charged into the reactor to rinse off any residual product left behind and then poured over the filter. The metallic blue silver nanoparticle cake was left in a fume hood overnight to air dry. The final yield was 7.51 g containing 83% silver (estimated from TGA analysis).

Comparative Example 1

Silver acetate was fully dissolved into a mixture of toluene and oleylamine at 50° C. Phenylhydrazine diluted in toluene was then added drop-wise followed by 30 minutes of mixing at the same temperature. The reaction solution was cooled down to room temperature. Next, a mixture of acetone and methanol (1:1 v/v) was added with stirring to precipitate the oleylamine-stabilized silver nanoparticles. The product was filtered and washed three times with acetone and methanol. The silver nanoparticles were then dissolved in toluene and oleic acid was added to the solution, followed by 30 minutes of mixing. Oleic acid-stabilized silver nanoparticles were precipitated by the addition of a mixture of acetone/methanol (1:1 v/v), filtered, washed with methanol 3 times, and vacuum dried at room temperature overnight. The final yield contained 65.6% silver (estimated from TGA analysis).

Results

The particle sizes of the silver nanoparticles were measured using transmission electron microscopy (TEM). ImagePro v6.2 image analysis software was used on the TEM images to determine the mean particle sizes.

The conductivity of films made from the silver nanoparticles was also measured. A silver nanoparticle solution was spin-coated on a glass substrate and annealed at 210° C. on a hotplate in air as needed (up to 30 minutes) to obtain a shiny thin silver film. The conductivity of the silver thin films was measured using a conventional four-probe technique.

The results are shown in Table 1.

TABLE 1

| Example | Particle size (nm)[1] | Conductivity ($\times 10^4$ S/cm) |
| --- | --- | --- |
| 1 | <10 | 2.3 |
| Comparative | <10 | 2.0 |

[1]Particle size includes stabilizer.

Figure 5:
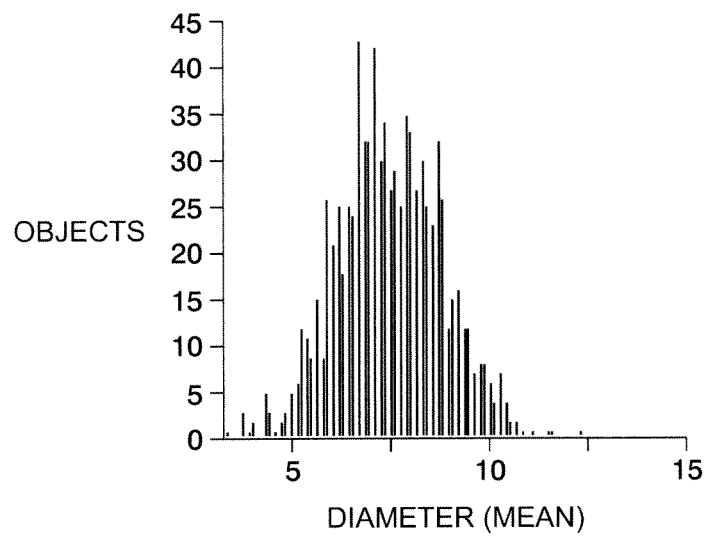
FIG. 5 is a graph showing the particle sizes and distributions of nanoparticles formed according to methods of the present disclosure.
Figure 6:
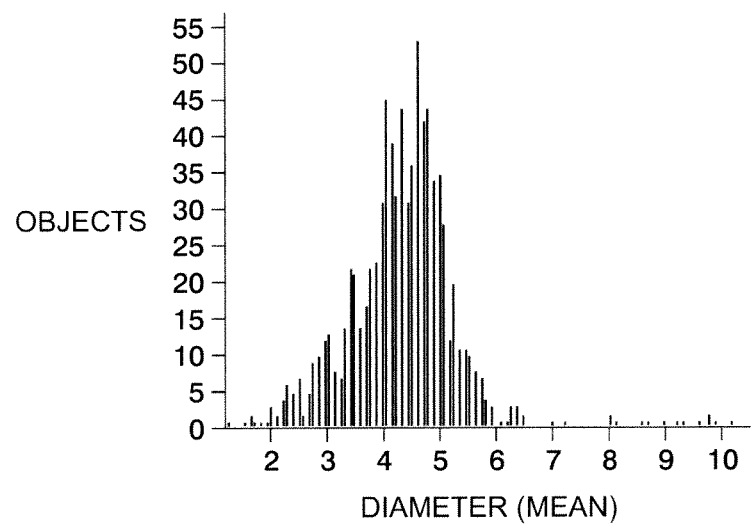
FIG. 6 is a graph showing the particle sizes and distributions of nanoparticles formed according to prior methods.

The particle size distribution for Example 1 is shown in FIG. 5, while the particle size distribution for Comparative Example 1 is shown in FIG. 6. The silver nanoparticles of the present disclosure have performance and particle size distributions similar to those made using prior methods.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A process for producing carboxylic acid-stabilized silver nanoparticles, comprising:
   forming a suspension of silver salt particles in a carboxylic acid, the carboxylic acid having at least 4 carbon atoms;
   forming a solution of an organohydrazine and a first organic solvent;
   heating the suspension;
   adding the solution to the suspension to form a mixture; and
   reacting the mixture to form carboxylic acid-stabilized silver nanoparticles, wherein the resulting nanoparticles have a silver content of 80 percent or more based on the weight of the carboxylic acid-stabilized silver nanoparticle;
   wherein the suspension consists of the silver salt particles and the carboxylic acid.

2. The process of claim 1, wherein the silver salt is selected from the group consisting of silver acetate, silver nitrate, silver oxide, silver acetylacetonate, silver benzoate, silver bromate, silver bromide, silver carbonate, silver chloride, silver citrate, silver fluoride, silver iodate, silver iodide, silver lactate, silver nitrite, silver perchlorate, silver phosphate, silver sulfate, silver sulfide, and silver trifluoroacetate.

3. The process of claim 1, wherein the carboxylic acid has from 4 to about 20 carbon atoms.

4. The process of claim 1, wherein the carboxylic acid is selected from the group consisting of butyric acid, pentanoic acid, hexanoic acid, heptanoic acid, octanoic acid, nonanoic acid, decanoic acid, undecanoic acid, dodecanoic acid, tridecanoic acid, myristic acid, pentadecanoic acid, palmitic acid, heptadecanoic acid, stearic acid, oleic acid, nonadecanoic acid, icosanoic acid, eicosenoic acid, elaidic acid, linoleic acid, and palmitoleic acid.

5. The process of claim 1, wherein the organohydrazine is of the formula:

$$R^6R^7N-NR^8R^9$$

wherein $R^6$, $R^7$, $R^8$ and $R^9$ are independently selected from hydrogen, alkyl, and aryl; and wherein at least one of $R^6$, $R^7$, $R^8$ and $R^9$ is not hydrogen.

6. The process of claim 1, wherein the organohydrazine is phenylhydrazine.

7. The process of claim 1, wherein the first organic solvent is selected from the group consisting of toluene, heptane, hexane, benzene, cyclohexane, pentane, bromobenzene, and chlorobenzene.

8. The process of claim 1, wherein the molar ratio of silver salt to carboxylic acid is from about 0.01 to about 1.

9. The process of claim 1, wherein the molar ratio of silver salt to organohydrazine is from about 0.5 to about 5.

10. The process of claim 1, wherein the molar ratio of carboxylic acid to organohydrazine is from about 5 to about 30.

11. The process of claim 1, wherein the mixture is heated at a temperature of from about 50° C. to about 100° C.

12. The process of claim 1, wherein the mixture is heated for a period of about 30 minutes or more.

13. The process of claim 1, wherein the resulting nanoparticles have an average diameter of from about 4 nanometers to about 10 nanometers.

14. The process of claim 1, wherein the resulting nanoparticles have a particle size distribution of from about 5 nanometers.

15. The process of claim 1, further comprising the steps of:
   separating the silver nanoparticles from the mixture with a non-solvent; and
   washing the silver nanoparticles.

16. The process of claim 15, wherein the non-solvent comprises acetone, methanol, ethanol, propanol, isopropanol, methyl ethyl ketone, acetonitrile, isobutyl alcohol, and combinations thereof.

17. A process for producing carboxylic acid-stabilized silver nanoparticles, comprising:
   forming a suspension of silver salt particles in a carboxylic acid having a first temperature, wherein the carboxylic acid is selected from the group consisting of butyric acid, pentanoic acid, hexanoic acid, heptanoic acid, octanoic acid, nonanoic acid, decanoic acid, undecanoic acid, dodecanoic acid, tridecanoic acid, myristic acid, pentadecanoic acid, palmitic acid, heptadecanoic acid, stearic acid, oleic acid, nonadecanoic acid, icosanoic acid, eicosenoic acid, elaidic acid, linoleic acid, and palmitoleic acid;
   forming a solution of an organohydrazine and a first organic solvent;
   adding the solution to the suspension to form a mixture;
   agitating the mixture;
   cooling the mixture to a second temperature; and
   adding a non-solvent to the mixture to obtain the carboxylic acid-stabilized silver nanoparticles, wherein the resulting nanoparticles have a silver content of 80 percent or more based on the weight of the carboxylic acid-stabilized silver nanoparticle;
   wherein the suspension consists of the silver salt particles and the carboxylic acid.

18. The process of claim 17, wherein the suspension is formed using silver acetate particles in oleic acid.

19. The process of claim 17, wherein the first temperature is about 80° C.

20. The process of claim 17, wherein the solution is formed using phenylhydrazine in toluene.

21. The process of claim 17, wherein the solution is added to the suspension over a period of about 30 minutes.

22. The process of claim 17, wherein the mixture is agitated for about 1 hour.

23. The process of claim 17, wherein the second temperature is 40° C. or lower.

24. The process of claim 17, wherein the non-solvent is a mixture of acetone and methanol.

25. The process of claim 17, wherein the mixture is maintained at the first temperature during agitation.

26. The process of claim 17, wherein the resulting nanoparticles have an average diameter of from about 4 nanometers to about 10 nanometers.

27. The process of claim 17, wherein the resulting nanoparticles have a particle size distribution of from about 5 nanometers.

28. The process of claim 17, wherein the resulting nanoparticles consist of (a) silver and (b) either (i) another metal or (ii) a non-metal selected from the group consisting of Si, C, and Ge.

* * * * *